(12) United States Patent
Liao et al.

(10) Patent No.: US 7,994,360 B2
(45) Date of Patent: Aug. 9, 2011

(54) BENZOFURAN COMPOUNDS

(75) Inventors: Yun Liao, Glen Rock, NJ (US); Youhong Hu, Ridgewood, NJ (US); Kenneth Nawoschik, Spring Valley, NY (US); Reza Fathi, Hohokus, NJ (US); Zhen Yang, Ridgewood, NJ (US); Yixin Liu, Paramus, NJ (US); Anthony Sandrasagra, Princeton, NJ (US)

(73) Assignee: XTL Biopharmaceuticals Ltd. (IL)

( * ) Notice: Subject to any disclaimer, the term of this patent is extended or adjusted under 35 U.S.C. 154(b) by 1329 days.

(21) Appl. No.: 11/130,660

(22) Filed: May 16, 2005

(65) Prior Publication Data

US 2006/0258682 A1    Nov. 16, 2006

(51) Int. Cl.
*C07C 69/00*    (2006.01)
*C07C 39/00*    (2006.01)

(52) U.S. Cl. .................. 560/138; 560/130; 568/716

(58) Field of Classification Search .............. 560/130, 560/138; 568/716
See application file for complete search history.

(56) References Cited

FOREIGN PATENT DOCUMENTS

| EP | 1506991 | 2/2005 |
|----|---------|--------|
| JP | 2002363261 | 12/2002 |
| WO | 2004/005264 | 1/2004 |
| WO | 2004/106328 | 12/2004 |
| WO | 2005/023818 | 3/2005 |

OTHER PUBLICATIONS

Godt et al. Chem,. Eur. J. 2000, vol. 6, No. 19, pp. 3522-3530.*
Rao et al. "Synthesis of Novel tyrosinyl FRET cassettes, terminators, and their potential use in DNA sequencing," Nucleosides, Nucleotides & Nucleic acids, 2003, vol. 22, Nos. 5-8 pp. 1443-1445.*
Yun Liao et al., "Palladium(II)-mediated cascade carbonylative annulation of o-alkynyl-phenos on silyl syntesis of a 2,3-disubstituted benzo[b]furan library." Organic Letters. Jul. 25, 2002, vol. 4, No. 15, pp. 2607-2609.
Database Beilstein, Belstein Crossfire Institut Zur Foerderung Der Chemischen Wissenschaften, DE; Citation No. 6524602, May 24, 2005.
Yun Liao et al., "Novel PdII-mediated cascade carboxylative annulation to construct benzo[b]furan-3-carboxylic acids." Organic Letters, Jun. 23, 2005, vol. 7, No. 13, pp. 2707-2709.
A.N. Grinev et al., "Search for Antiviral Activity Among 4 hydoxybenzofuran Derivatives" Database Biosis, Biosciences Information Service, Philadelphia, PA; 1987.
Kimiko-Farmatsevticheskii Zhurnal, vol. 21, No. 11, 1987, pp. 1318-1320.
A. Godt et al., "Synthesis of 3,5-disubstituted 4-hydroxybenzoates by aryl-aryl and alkynyl-aryl coupling" Journal of Organic Chemistry, May 5, 2000, vol. 65, No. 9, pp. 2837-2842.
A. Godt, "Synthesis of Unsymmetical 1,4-Diarylbutadiynes by Stille Coupling" Journal of Organic Chemistry, American Chemical Society, vol. 62, 1997, pp. 7471-7474.
M. Ayabe et al. "Construction of Monmeric and Polymeric Porphyrin Compartments by a Pd(II)-pyridine Interaction and Their Chiral Twisting by a BINAP ligand" Journal of Organic Chemistry, vol. 68 No. 3, Feb. 7, 2003, pp. 1059-1066.
Database Beilstein, Belstein Crossfire Institut Zue Foerderung Der Chemischen Wissenschaften, DE; BRN 2158220, 1997.
Database Beilstein, Belstein Crossfire Institut Zue Foerderung Der Chemischen Wissenschaften, DE; BRN 9670676, 2003.
Qinghui Chu, et al., "Synthesis and Optical Properties of Poly[(2-alkoxy-5-methyl-1,3-phenyleneethylene)-alt-(1,3-phenyleneethynylene)]s" Synthesis, (9), 1261-1267.
M. Pattarawareapan et al., "A Linker Scaffold to Present Dimers of Pharmacophres Prepared by Solid-Phase Synthesis" Angewandte Chemie, International Edition, vol. 39, No. 23, Dec. 4, 2000, pp. 4299-4301.
A. Godt et al., "Formation, Structure and Confirmational Dynamics of Highly Substituted Diphenylcarbonates" Database Accession No. 2000: 743151.
M. Pattarawareapan et al., "A Rigid Linker-Scaffold for Solid-Phase Synthesis of Dimeric Pharmacophores" Journal of Combinatorial Chemistry 3(1), 102-116.
Masahide Tominaga et al., "24-Fold Endohedral Functionalization of a Self-Assembled $M_{12}L_{24}$ Coordination Nanoball" Journal of the American Chemical Society, Aug. 31, 2005, col. 127, No. 34, pp. 11950-11951.
European Examination Report, European Application No. 06770417.1, Jul. 6, 2009, 3 pages.
Liao, Y. et al., "The Palladium (II)-Mediated Cascade Carbonylative Annulation of o-Alkynylphenols on a Silyl Linker Based Macrobeads: a Combinatorial Synthesis of a 2,3-Disubstituted Benzo[b]furan Library," American Chemical Society, Org. Lett., 2002, 160 pages.
PCT International Search Report, PCT Application No. PCT/US2006/018866, Mailed Mar. 27, 2007, Completed Oct. 13, 2006, 8 pages.
PCT Written Opinion, PCT Application No. PCT/US2006/018866, Mailed Mar. 27, 2007, Completed Oct. 13, 2006, 9 pages.

* cited by examiner

*Primary Examiner* — Shengjun Wang
(74) *Attorney, Agent, or Firm* — Fenwick & West LLP

(57) ABSTRACT

The present invention relates to benzofuran derivatives for use in antiviral compositions. More specifically, the present invention relates to compositions and methods for the treatment of hepatitis C virus by administering the benzofuran derivatives in a therapeutically effective amount.

1 Claim, No Drawings

BENZOFURAN COMPOUNDS

BACKGROUND OF THE INVENTION

Strategies in new drug discovery often look to natural products for leads in finding new chemical compounds with therapeutic properties. One of the recurring problems in drug discovery is the availability of organic compounds derived from natural sources. Techniques employing combinatorial chemistry attempt to overcome this problem by allowing the high throughput synthesis and testing of hundreds or thousands of related synthetic compounds, called a chemical library. In designing the synthesis of a prospective therapeutic compound or a chemical library, one often looks to natural chemical motifs which are known to have broad biological activity. Benzofuran derivatives are of particular interest due to their frequent occurrence in nature and range of biological activities. Benzofuran is named and numbered according to the Ring Index, American Chemical Society, as follows

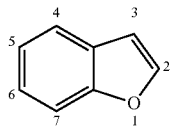

Infection with the Hepatitis C virus (HCV) represents a serious world-wide health crisis. In more than 70% of infected individuals, the virus evades clearance by the immune system leading to a persistent HCV infection. The long term effects of persistent HCV infection range from an apparently healthy carrier state to chronic hepatitis, liver fibrosis, cirrhosis, and eventually hepatocellular carcinoma. HCV is a leading cause of chronic liver disease. The best therapy currently available for treatment of HCV infection uses a combination of pegylated α-interferon and ribavirin. However, many of the patients treated with this therapy fail to show a sufficient antiviral response. Additionally, interferon treatment also induces severe side-effects (i.e. retinopathy, thyroiditis, acute pancreatitis, depression) that diminish the quality of life of treated patients. Thus, it is vital that more effective treatments be identified.

SUMMARY OF THE INVENTION

The present invention provides a compound of the formula I:

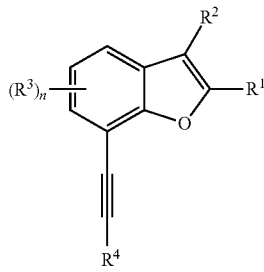

(I)

wherein:
$R^1$ is selected from the group consisting of alkyl, cycloalkyl, alkenyl, alkynyl, aralkyl, aryl, heteroaryl, —(CH$_2$)$_a$C(O)(CH$_2$)$_b$R$^{11}$, —(CH$_2$)$_a$C(O)N(R$^{12}$)(R$^{13}$), —(CH$_2$)$_a$C(O)O(CH$_2$)$_b$R$^{11}$, —(CH$_2$)$_a$C(O)N(R$^{12}$)(R$^{13}$), and —(CH$_2$)$_a$N(R$^{12}$)(R$^{13}$), $R^{11}$ is selected from H, alkyl, cycloalkyl, cycloalkenyl, heterocycloalkyl, alkenyl, alkynyl, aralkyl, aryl and heteroaryl;

$R^{12}$ and $R^{13}$ are independently selected from H, alkyl, cycloalkyl, cycloalkenyl, heterocycloalkyl, alkenyl, alkynyl, aralkyl, aryl and heteroaryl;

or $R^{12}$ and $R^{13}$ may be taken together with the nitrogen to which they are attached form a 5- to 7-membered ring which may optionally contain a further heteroatom;

a is 0 to 6;
b is 0 to 6;

$R^2$ is selected from the group consisting of alkyl, cycloalkyl, alkenyl, alkynyl, aralkyl, aryl, heteroaryl, —(CH$_2$)$_c$C(O)(CH$_2$)$_d$R$^{21}$, —(CH$_2$)$_c$C(O)N(R$^{22}$)(R$^{23}$), —(CH$_2$)$_c$C(O)O(CH$_2$)$_d$R$^{21}$, and —(CH$_2$)$_c$C(O)N(R$^{22}$)(R$^{23}$), each $R^{21}$ is independently selected from H, alkyl, cycloalkyl, cycloalkenyl, heterocycloalkyl, alkenyl, alkynyl, aralkyl, aryl and heteroaryl;

$R^{22}$ and $R^{23}$ are independently selected from H, alkyl, cycloalkyl, cycloalkenyl, heterocycloalkyl, alkenyl, alkynyl, aralkyl, aryl and heteroaryl;

or $R^{22}$ and $R^{23}$ may be taken together with the nitrogen to which they are attached form a 5- to 7-membered ring which may optionally contain a further heteroatom;

c is 0 to 6;
d is 0 to 6;

$R^3$ is selected from the group consisting of halo, alkyl, CN, NO$_2$, CO$_2$R$^{31}$, C(O)R$^{31}$, —O—R$^{31}$, —N(R$^{32}$)(R$^{33}$), —N(R$^{31}$)C(O)R$^{31}$, —N(R$^{31}$)SO$_2$R$^{31}$, —SR$^{31}$, —C(O)N(R$^{32}$)(R$^{33}$), —OC(O)R$^{31}$, —OC(O)N(R$^{32}$)(R$^{33}$), SO$_2$, —SOR$^{31}$, —SO$_3$R$^{31}$, —SO$_2$N(R$^{32}$)(R$^{33}$), cycloalkyl, cycloalkenyl, heterocycloalkyl, aralkyl, aryl and heteroaryl, each $R^{31}$ is independently selected from H, alkyl, cycloalkyl, cycloalkenyl, alkenyl, alkynyl, aralkyl, aryl and heteroaryl;

$R^{32}$ and $R^{33}$ are independently selected from H, alkyl, cycloalkyl, cycloalkenyl, alkenyl, alkynyl, aralkyl, aryl and heteroaryl;

or $R^{32}$ and $R^{33}$ may be taken together with the nitrogen to which they are attached form a 5- to 7-membered ring which may optionally contain a further heteroatom;

or $R^3$ is a group of the formula

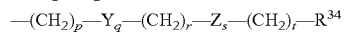

wherein Y and Z are independently selected from O, S, —OCH$_2$CH$_2$O—, —C(R$^{36}$)$_2$C(O)—

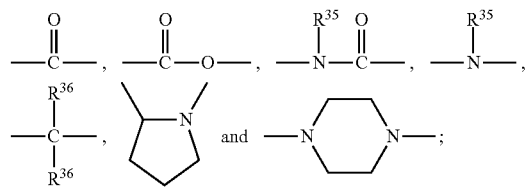

p, r and t are independently selected from values from 0 to 10;
q and s are independently selected from 0 and 1, provided that when t=0 then s=0, and when r=0 then q=0; and
$R^{34}$ is selected from OR$^{35}$, CO$_2$R$^{35}$, —NH—CO$_2$R$^{35}$, —NHC(O)—CH$_2$OR$^{35}$ and

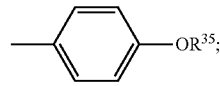

each $R^{35}$ is independently selected from the group consisting of H, alkyl, alkenyl, alkynyl, cycloalkyl, heterocycloalkyl, aralkyl, aryl and heteroaryl;

each $R^{36}$ is independently selected from the group consisting of H, alkyl, alkenyl, alkynyl, cycloalkyl, heterocycloalkyl aralkyl, aryl, heteroaryl; $CO_2R^{37}$, $C(O)R^{37}$, —O—$R^{37}$, —N($R^{37}$)($R^{37}$), —N($R^{37}$)C(O)$R^{37}$, —N($R^{37}$)$SO_2R^{37}$, —C(O)N($R^{37}$)($R^{37}$), —OC(O)$R^{37}$, and —OC(O)N($R^{37}$)($R^{37}$);

$R^{37}$ is selected from H, alkyl, alkenyl, alkynyl, cycloalkyl, heterocycloalkyl, aralkyl, aryl and heteroaryl n is selected from 0-4, and m is 0 or 1, with the proviso that the sum of n plus m does not exceed 4;

$R^4$ is selected from the group consisting of alkyl, cycloalkyl, heterocycloalkyl, alkenyl, alkynyl, aralkyl, aryl, heteroaryl, —$(CH_2)_eC(O)(CH_2)_fR^{41}$, —$(CH_2)_eC(O)N(R^{42})(R^{43})$, —$(CH_2)_eC(O)O(CH_2)_fR^{41}$, —$(CH_2)_eC(O)N(R^{42})(R^{43})$, and —$(CH_2)_eN(R^{42})(R^{43})$, each $R^{41}$ is independently selected from H, alkyl, cycloalkyl, cycloalkenyl, heterocycloalkyl, alkenyl, alkynyl, aralkyl, aryl and heteroaryl;

$R^{42}$ and $R^{43}$ are independently selected from H, alkyl, cycloalkyl, cycloalkenyl, heterocycloalkyl, alkenyl, alkynyl, aralkyl, aryl and heteroaryl;

or $R^{42}$ and $R^{43}$ may be taken together with the nitrogen to which they are attached form a 5- to 7-membered ring which may optionally contain a further heteroatom;

e is 1 to 6;

f is 1 to 6;

or a pharmaceutically acceptable salt or hydrate thereof.

The invention also provides a synthetic process for the preparation of compounds of the formula I. The process uses mild reaction conditions, which provides a high substituent tolerance. Thus, the process is applicable to the preparation of a wide variety of benzofuran derivatives with diverse substitution patterns. Additionally, the process is appropriate for use with combinatorial synthesis techniques. Thus, the process provides a method for producing a library of benzofuran derivatives for biological screening.

The invention also provides compositions and methods for the treatment of HCV by administering a compound of the present invention in a therapeutically effective amount.

DETAILED DESCRIPTION OF THE INVENTION

The term "halo" or "halogen" as used herein includes fluorine, chlorine, bromine and iodine.

The term "alkyl" as used herein contemplates substituted or unsubstituted, straight and branched chain alkyl radicals containing from one to fifteen carbon atoms. The term "lower alkyl" as used herein contemplates both straight and branched chain alkyl radicals containing from one to six carbon atoms and includes methyl, ethyl, propyl, isopropyl, butyl, isobutyl, tert-butyl, and the like. The alkyl group may be optionally substituted with one or more substituents selected from halo, CN, $NO_2$, $CO_2R$, C(O)R, —O—R, —N(R')(R"), —N(R)C(O)R, —N(R)$SO_2R$, —SR, —C(O)N(R')(R"), —OC(O)R, —OC(O)N(R')(R"), $SO_2$, —SOR, —$SO_3R$, —$SO_2N(R')(R")$, halo, cycloalkyl, cycloalkenyl, aryl and heteroaryl.

The term "alkenyl" as used herein contemplates substituted or unsubstituted, straight and branched chain alkene radicals containing from two to 8 carbon atoms. The alkenyl group may be optionally substituted with one or more substituents selected from halo, CN, $NO_2$, $CO_2R$, C(O)R, —O—R, —N(R')(R"), —N(R)C(O)R, —N(R)$SO_2R$, —SR, —C(O)N(R')(R"), —OC(O)R, —OC(O)N(R')(R"), $SO_2$, —SOR, —$SO_3R$, —$SO_2N(R')(R")$, halo, cycloalkyl, cycloalkenyl, aryl and heteroaryl.

The term "alkynyl" as used herein contemplates substituted or unsubstituted, straight and branched carbon chain containing from two to 8 carbon atoms and having at least one carbon-carbon triple bond. The term alkynyl includes, for example ethynyl, 1-propynyl, 2-propynyl, 1-butynyl, 3-methyl-1-butynyl, and the like. The alkynyl group may be optionally substituted with one or more substituents selected from halo, CN, $NO_2$, $CO_2R$, C(O)R, —O—R, —N(R')(R"), —N(R)C(O)R, —N(R)$SO_2R$, —SR, —C(O)N(R')(R"), —OC(O)R, —OC(O)N(R')(R"), $SO_2$, —SOR, —$SO_3R$, —$SO_2N(R')(R")$, halo, cycloalkyl, cycloalkenyl, aryl and heteroaryl.

The term "cycloalkyl" as used herein contemplates substituted or unsubstituted cyclic alkyl radicals containing form 3 to 7 carbon atoms and includes cyclopropyl, cyclopentyl, cyclohexyl, and the like. The cycloalkyl group may be optionally substituted with one or more substituents selected from halo, CN, $NO_2$, $CO_2R$, C(O)R, —O—R, —N(R')(R"), —N(R)C(O)R, —N(R)$SO_2R$, —SR, —C(O)N(R')(R"), —OC(O)R, —OC(O)N(R')(R"), $SO_2$, —SOR, —$SO_3R$, —$SO_2N(R')(R")$, halo, alkyl, cycloalkenyl, aryl and heteroaryl.

The term "cycloalkenyl" as used herein contemplates substituted or unsubstituted cyclic alkenyl radicals containing form 5 to 7 carbon atoms in which has a double bond between two of the ring carbons and includes cyclopentenyl, cyclohexenyl, and the like. The cycloalkenyl group may be optionally substituted with one or more substituents selected from halo, CN, $NO_2$, $CO_2R$, C(O)R, —O—R, —N(R')(R"), —N(R)C(O)R, —N(R)$SO_2R$, —SR, —C(O)N(R')(R"), —OC(O)R, —OC(O)N(R')(R"), $SO_2$, —SOR, —$SO_3R$, —$SO_2N(R')(R")$, halo, alkyl, cycloalkenyl, aryl and heteroaryl.

The term "aralkyl" as used herein contemplates a lower alkyl group which has as a substituent an aromatic group, which aromatic group may be substituted or unsubstituted. The aralkyl group may be optionally substituted with one or more substituents selected from halo, CN, $NO_2$, $CO_2R$, C(O)R, —O—R, —N(R')(R"), —N(R)C(O)R, —N(R)$SO_2R$, —SR, —C(O)N(R')(R"), —OC(O)R, —OC(O)N(R')(R"), $SO_2$, —SOR, —$SO_3R$, —$SO_2N(R')(R")$, halo, cycloalkyl, cycloalkenyl, aryl and heteroaryl.

The term "heterocyclic group" or "heterocyclic ring" as used herein contemplates substituted or unsubstituted aromatic and non-aromatic cyclic radicals having at least one heteroatom as a ring member. Preferred heterocyclic groups are those containing 5 or 6 ring atoms which includes at least one hetero atom, and includes cyclic amines such as morpholino, piperidino, pyrrolidino, and the like, and cyclic ethers, such as tetrahydrofuran, tetrahydropyran, and the like. Aromatic heterocyclic groups, also termed "heteroaryl" groups contemplates single-ring hetero-aromatic groups that may include from one to three heteroatoms, for example, pyrrole, furan, thiophene, imidazole, oxazole, thiazole, triazole, pyrazole, pyridine, pyrazine, pyridazine, pyrimidine, and the like. The term heteroaryl also includes polycyclic hetero-aromatic systems having two or more rings in which two atoms are common to two adjoining rings (the rings are "fused") wherein at least one of the rings is a heteroaryl, e.g., the other rings can be cycloalkyls, cycloalkenyls, aryl, heterocycles and/or heteroaryls. Examples of polycyclic heteroaromatic systems include quinoline, isoquinoline, tetrahydroisoquinoline, quinoxaline, quinaxoline, benzimidazole, benzofuran, purine, imidazopyridine, benzotriazole, and the like. The heterocyclic group may be optionally substituted with one or more substituents selected from halo, alkyl, CN, $NO_2$, $CO_2R$, C(O)R, —O—R, —N(R')(R"), —N(R)C(O)R, —N(R)$SO_2R$, —SR, —C(O)N(R')(R"), —OC(O)R, —OC(O)N(R')(R"), $SO_2$, —SOR, —$SO_3R$, —$SO_2N(R')(R")$, halo, cycloalkyl, cycloalkenyl, aryl and heteroaryl.

The term "heterocycloalkyl" as used herein contemplates substituted or unsubstituted non-aromatic cyclic radicals having at least one heteroatom as a ring member. Preferred heterocycloalkyl groups are those containing 5 or 6 ring atoms which includes at least one hetero atom, and includes cyclic amines such as morpholino, piperidino, pyrrolidino, and the like, and cyclic ethers, such as tetrahydrofuran, tetrahydropyran, and the like. Cyclic ethers also includes cyclic sugars, which may have protecting groups on one or more of the hydroxyls. The term heterocycloalkyl also includes polycyclic hetero-aromatic systems having two or more rings in which two atoms are common to two adjoining rings (the rings are "fused"). The heterocycloalkyl group may be optionally substituted with one or more substituents selected from halo, alkyl, CN, $NO_2$, $CO_2R$, $C(O)R$, —O—R, —N(R')(R''), —N(R)C(O)R, —N(R)$SO_2$R, —SR, —C(O)N(R')(R''), —OC(O)R, —OC(O)N(R')(R''), $SO_2$, —SOR, —$SO_3R$, —$SO_2$N(R')(R''), halo, cycloalkyl, cycloalkenyl, aryl and heteroaryl.

The terms "aryl", "aromatic group", or "aromatic ring" as used herein contemplates substituted or unsubstituted single-ring aromatic groups (for example, phenyl, pyridyl, pyrazole, etc.) and polycyclic ring systems (naphthyl, quinoline, etc.). The polycyclic rings may have two or more rings in which two atoms are common to two adjoining rings (the rings are "fused") wherein at least one of the rings is aromatic, e.g., the other rings can be cycloalkyls, cycloalkenyls, aryl, heterocycles and/or heteroaryls. The aryl group may be optionally substituted with one or more substituents selected from halo, alkyl, CN, $NO_2$, $CO_2R$, $C(O)R$, —O—R, —N(R')(R''), —N(R)C(O)R, —N(R)$SO_2$R, —SR, —C(O)N(R')(R''), —OC(O)R, —OC(O)N(R')(R''), $SO_2$, —SOR, —$SO_3R$, —$SO_2$N(R')(R''), halo, cycloalkyl, cycloalkenyl, aryl and heteroaryl.

Each R is independently selected from H, alkyl, cycloalkyl, alkenyl, alkynyl, aralkyl, aryl and heteroaryl. Each R' and R'' are independently selected from H, alkyl, cycloalkyl, alkenyl, alkynyl, aralkyl, aryl and heteroaryl; or R' and R'' may be taken together with the nitrogen to which they are attached form a 5- to 7-membered ring which may optionally contain a further heteroatom, The term "heteroatom", particularly as a ring heteroatom, refers to N, O, and S.

All value ranges, for example those given for n and m, are inclusive over the entire range. Thus, a range of 0 to 4 would include the values 0, 1, 2, 3 and 4.

The present invention provides benzofuran derivatives of the formula I:

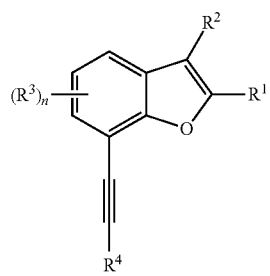

(I)

wherein:
$R^1$ is selected from the group consisting of alkyl, cycloalkyl, alkenyl, alkynyl, aralkyl, aryl, heteroaryl, —$(CH_2)_aC(O)$ $(CH_2)_bR^{11}$, —$(CH_2)_aC(O)N(R^{12})(R^{13})$, —$(CH_2)_aC(O)O$ $(CH_2)_bR^{11}$, —$(CH_2)_aC(O)N(R^{12})(R^{13})$, and —$(CH_2)_aN(R^{12})(R^{13})$, $R^{11}$ is selected from H, alkyl, cycloalkyl, cycloalkenyl, heterocycloalkyl, alkenyl, alkynyl, aralkyl, aryl and heteroaryl;

$R^{12}$ and $R^{13}$ are independently selected from H, alkyl, cycloalkyl, cycloalkenyl, heterocycloalkyl, alkenyl, alkynyl, aralkyl, aryl and heteroaryl;

or $R^{12}$ and $R^{13}$ may be taken together with the nitrogen to which they are attached form a 5- to 7-membered ring which may optionally contain a further heteroatom;

a is 0 to 6;
b is 0 to 6;
$R^2$ is selected from the group consisting of alkyl, cycloalkyl, alkenyl, alkynyl, aralkyl, aryl, heteroaryl, —$(CH_2)_cC(O)$ $(CH_2)_dR^{21}$, —$(CH_2)_cC(O)N(R^{22})(R^{23})$, —$(CH_2)_cC(O)O$ $(CH_2)_dR^{21}$, and —$(CH_2)_cC(O)N(R^{22})(R^{23})$, each $R^{21}$ is independently selected from H, alkyl, cycloalkyl, cycloalkenyl, heterocycloalkyl, alkenyl, alkynyl, aralkyl, aryl and heteroaryl;

$R^{22}$ and $R^{23}$ are independently selected from H, alkyl, cycloalkyl, cycloalkenyl, heterocycloalkyl, alkenyl, alkynyl, aralkyl, aryl and heteroaryl;

or $R^{22}$ and $R^{23}$ may be taken together with the nitrogen to which they are attached form a 5- to 7-membered ring which may optionally contain a further heteroatom;

c is 0 to 6;
d is 0 to 6;
$R^3$ is selected from the group consisting of halo, alkyl, CN, $NO_2$, $CO_2R^{31}$, $C(O)R^{31}$, —O—$R^{31}$, —N($R^{32}$)($R^{33}$), —N($R^{31}$)C(O)$R^{31}$, —N($R^{31}$)$SO_2R^{31}$, —$SR^{31}$, —C(O)N($R^{32}$)($R^{33}$), —OC(O)$R^{31}$, —OC(O)N($R^{32}$)($R^{33}$), $SO_2$, —$SOR^{31}$, —$SO_3R^{31}$, —$SO_2$N($R^{32}$)($R^{33}$), cycloalkyl, cycloalkenyl, heterocycloalkyl, aralkyl, aryl and heteroaryl, each $R^{31}$ is independently selected from H, alkyl, cycloalkyl, cycloalkenyl, alkenyl, alkynyl, aralkyl, aryl and heteroaryl;

$R^{32}$ and $R^{33}$ are independently selected from H, alkyl, cycloalkyl, cycloalkenyl, alkenyl, alkynyl, aralkyl, aryl and heteroaryl;

or $R^{32}$ and $R^{33}$ may be taken together with the nitrogen to which they are attached form a 5- to 7-membered ring which may optionally contain a further heteroatom; or $R^3$ is a group of the formula

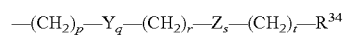

wherein Y and Z are independently selected from O, S, —$OCH_2CH_2O$—, —$C(R^{36})_2C(O)$—

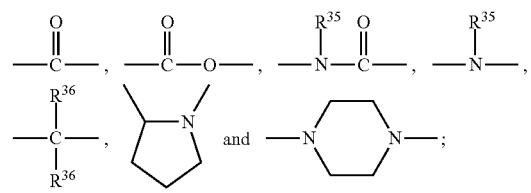

p, r and t are independently selected from values from 0 to 10;
q and s are independently selected from 0 and 1, provided that when t=0 then s=0, and when r=0 then q=0; and $R^{34}$ is selected from $OR^{35}$, $CO_2R^{35}$, —NH—$CO_2R^{35}$, —NHC(O)—$CH_2OR^{35}$ and

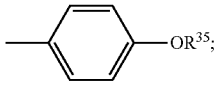

each $R^{35}$ is independently selected from the group consisting of H, alkyl, alkenyl, alkynyl, cycloalkyl, heterocycloalkyl, aralkyl, aryl and heteroaryl;
each $R^{36}$ is independently selected from the group consisting of H, alkyl, alkenyl, alkynyl, cycloalkyl, heterocycloalkyl aralkyl, aryl, heteroaryl; $CO_2R^{37}$, $C(O)R^{37}$, —O—$R^{37}$, —N($R^{37}$)($R^{37}$), —N($R^{37}$)C(O)$R^{37}$, —N($R^{37}$)$SO_2R^{37}$, —C(O)N($R^{37}$)($R^{37}$), —OC(O)$R^{37}$, and —OC(O)N($R^{37}$)($R^{37}$);
$R^{37}$ is selected from H, alkyl, alkenyl, alkynyl, cycloalkyl, heterocycloalkyl, aralkyl, aryl and heteroaryl
n is selected from 0-4, and
m is 0 or 1, with the proviso that the sum of n plus m does not exceed 4;
$R^4$ is selected from the group consisting of alkyl, cycloalkyl, heterocycloalkyl, alkenyl, alkynyl, aralkyl, aryl, heteroaryl, —$(CH_2)_eC(O)(CH_2)_fR^{41}$, —$(CH_2)_eC(O)N(R^{42})(R^{43})$, —$(CH_2)_eC(O)O(CH_2)_fR^{41}$, —$(CH_2)_eC(O)N(R^{42})(R^{43})$, and —$(CH_2)_eN(R^{42})(R^{43})$,
each $R^{41}$ is independently selected from H, alkyl, cycloalkyl, cycloalkenyl, heterocycloalkyl, alkenyl, alkynyl, aralkyl, aryl and heteroaryl;
$R^{42}$ and $R^{43}$ are independently selected from H, alkyl, cycloalkyl, cycloalkenyl, heterocycloalkyl, alkenyl, alkynyl, aralkyl, aryl and heteroaryl;
or $R^{42}$ and $R^{43}$ may be taken together with the nitrogen to which they are attached form a 5- to 7-membered ring which may optionally contain a further heteroatom;
e is 1 to 6;
f is 1 to 6;
or a pharmaceutically acceptable salt or hydrate thereof.
When Y or Z are ester and amide functionalities,

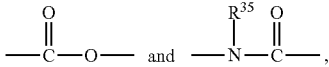

the group may be in either available orientation. Thus, for example, when Y is

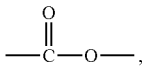

then $R^3$ may be chosen from

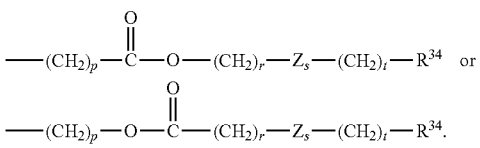

In a preferred embodiment of the invention, $R^2$ of a compound of the formula I is selected to be —C(O)O—$R^{21}$ to give a compound of the formula II:

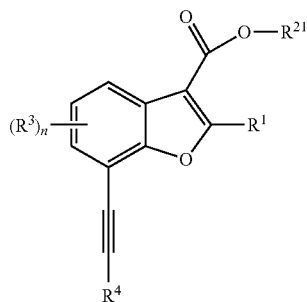

wherein:
$R^1$ is selected from the group consisting of alkyl, cycloalkyl, alkenyl, alkynyl, aralkyl, aryl, heteroaryl, —$(CH_2)_aC(O)(CH_2)_bR^{11}$, —$(CH_2)_1C(O)N(R^{12})(R^{13})$, —$(CH_2)_aC(O)O(CH_2)_bR^{11}$, —$(CH_2)_aC(O)N(R^{12})(R^{13})$, and —$(CH_2)_aN(R^{12})(R^{13})$,
$R^{11}$ is selected from H, alkyl, cycloalkyl, cycloalkenyl, heterocycloalkyl, alkenyl, alkynyl, aralkyl, aryl and heteroaryl;
$R^{12}$ and $R^{13}$ are independently selected from H, alkyl, cycloalkyl, cycloalkenyl, heterocycloalkyl, alkenyl, alkynyl, aralkyl, aryl and heteroaryl;
or $R^{12}$ and $R^{13}$ may be taken together with the nitrogen to which they are attached form a 5- to 7-membered ring which may optionally contain a further heteroatom;
a is 0 to 6;
b is 0 to 6;
$R^{21}$ is independently selected from H, alkyl, cycloalkyl, cycloalkenyl, heterocycloalkyl, alkenyl, alkynyl, aralkyl, aryl and heteroaryl;
$R^3$ is selected from the group consisting of halo, alkyl, CN, $NO_2$, $CO_2R^{31}$, $C(O)R^{31}$, —O—$R^{31}$, —N($R^{32}$)($R^{33}$), —N($R^{31}$)C(O)$R^{31}$, —N($R^{31}$)$SO_2R^{31}$, —$SR^{31}$, —C(O)N($R^{32}$)($R^{33}$), —OC(O)$R^{31}$, —OC(O)N($R^{32}$)($R^{33}$), $SO_2$, —$SOR^{31}$, —$SO_3R^{31}$, —$SO_2N(R^{32})(R^{33})$, cycloalkyl, cycloalkenyl, heterocycloalkyl, aralkyl, aryl and heteroaryl,
each $R^{31}$ is independently selected from H, alkyl, cycloalkyl, cycloalkenyl, alkenyl, alkynyl, aralkyl, aryl and heteroaryl;
$R^{32}$ and $R^{33}$ are independently selected from H, alkyl, cycloalkyl, cycloalkenyl, alkenyl, alkynyl, aralkyl, aryl and heteroaryl;
or $R^{32}$ and $R^{33}$ may be taken together with the nitrogen to which they are attached form a 5- to 7-membered ring which may optionally contain a further heteroatom; or $R^3$ is a group of the formula

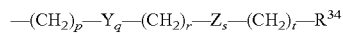

wherein Y and Z are independently selected from O, S, —$OCH_2CH_2O$—, —$C(R^{36})_2C(O)$—

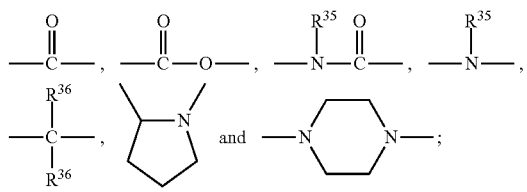

p, r and t are independently selected from values from 0 to 10;

q and s are independently selected from 0 and 1, provided that when t=0 then s=0, and when r=0 then q=0; and $R^{34}$ is selected from $OR^{35}$, $CO_2R^{35}$, —NH—$CO_2R^{35}$, —NHC(O)—$CH_2OR^{35}$ and

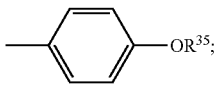

each $R^{35}$ is independently selected from the group consisting of H, alkyl, alkenyl, alkynyl, cycloalkyl, heterocycloalkyl, aralkyl, aryl and heteroaryl;

each $R^{36}$ is independently selected from the group consisting of H, alkyl, alkenyl, alkynyl, cycloalkyl, heterocycloalkyl aralkyl, aryl, heteroaryl; $CO_2R^{37}$, $C(O)R^{37}$, —O—$R^{37}$, —N($R^{37}$)($R^{37}$), —N($R^{37}$)C(O)$R^{37}$, —N($R^{37}$)$SO_2R^{37}$, —C(O)N($R^{37}$)($R^{37}$), —OC(O)$R^{37}$, and —OC(O)N($R^{37}$)($R^{37}$);

$R^{37}$ is selected from H, alkyl, alkenyl, alkynyl, cycloalkyl, heterocycloalkyl, aralkyl, aryl and heteroaryl n is selected from 0-4, and m is 0 or 1, with the proviso that the sum of n plus m does not exceed 4;

$R^4$ is selected from the group consisting of alkyl, cycloalkyl, heterocycloalkyl, alkenyl, alkynyl, aralkyl, aryl, heteroaryl, —$(CH_2)_eC(O)(CH_2)_fR^{41}$, —$(CH_2)_eC(O)N(R^{42})(R^{43})$, —$(CH_2)_eC(O)O(CH_2)_fR^{41}$, —$(CH_2)_eC(O)N(R^{42})(R^{43})$, and —$(CH_2)_eN(R^{42})(R^{43})$, each $R^{41}$ is independently selected from H, alkyl, cycloalkyl, cycloalkenyl, heterocycloalkyl, alkenyl, alkynyl, aralkyl, aryl and heteroaryl;

$R^{42}$ and $R^{43}$ are independently selected from H, alkyl, cycloalkyl, cycloalkenyl, heterocycloalkyl, alkenyl, alkynyl, aralkyl, aryl and heteroaryl;

or $R^{42}$ and $R^{43}$ may be taken together with the nitrogen to which they are attached form a 5- to 7-membered ring which may optionally contain a further heteroatom;

e is 1 to 6;

f is 1 to 6;

or a pharmaceutically acceptable salt or hydrate thereof.

In a preferred embodiment of the invention, $R^1$ and $R^4$ are selected to be the same for compounds of the formula I or of the formula II.

Table 1 provides representative embodiments for compounds of the formula II.

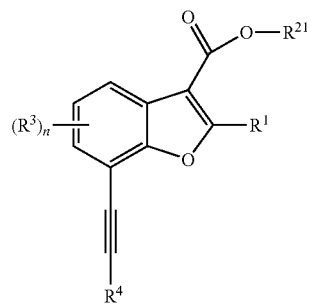

| no. | $R^1$ | $R^{21}$ | $R^3$ | $R^4$ |
|---|---|---|---|---|
| 22258 | —$(CH_2)_3CH_3$ | —$(CH_2)_3$—⟨C_6H_4⟩—$OCH_3$ | HO—(CH_2)_3—NH—C(O)—CH(Ph)—CH_2—  5- | —$(CH_2)_3CH_3$ |
| 22237 | —$(CH_2)_4CH_3$ | —$(CH_2)_4CH$=$CH_2$ | HO—(CH_2)_3—NH—C(O)—CH(Ph)—CH_2—  5- | —$(CH_2)_4CH_3$ |
| 22266 | —$(CH_2)_3CH_3$ | (diacetonide sugar structure) | HO—(CH_2)_3—NH—C(O)—CH(Ph)—CH_2—  5- | —$(CH_2)_3CH_3$ |

-continued

| no. | $R^1$ | $R^{21}$ | $R^3$ | $R^4$ |
|---|---|---|---|---|
| 22288 | —$(CH_2)_3Cl$ | —$CH_2CF_3$ | 5- (structure: HO-phenyl-piperazine-C(O)-CH(NHAc)-CH2-) | —$(CH_2)_3Cl$ |
| 35983 | —$(CH_2)_3CH_3$ | —$(CH_2)_4CH=CH_2$ | 5- (structure: HO-CH2-CH(CH2Ph)-NH-C(O)-CH(Ph)-) | —$(CH_2)_3CH_3$ |
| 35759 | —$CH_2$-Ph | —$(CH_2)_2CH(CH_3)_2$ | 5- (structure: HO-CH2-CH(iPr)-NH-C(O)-CH(Ph)-) | —$CH_2$-Ph |

In a another embodiment of the invention, there is provided a compound having the formula III:

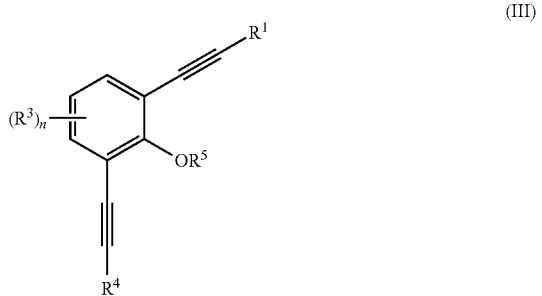

(III)

wherein:

$R^1$ is selected from the group consisting of alkyl, cycloalkyl, alkenyl, alkynyl, aralkyl, aryl, heteroaryl, —$(CH_2)_aC(O)(CH_2)_bR^{11}$, —$(CH_2)_aC(O)N(R^{12})(R^{13})$, —$(CH_2)_aC(O)O(CH_2)_bR^{11}$, —$(CH_2)_aC(O)N(R^{12})(R^{13})$, and —$(CH_2)_aN(R^{12})(R^{13})$, $R^{11}$ is selected from H, alkyl, cycloalkyl, cycloalkenyl, heterocycloalkyl, alkenyl, alkynyl, aralkyl, aryl and heteroaryl;

$R^{12}$ and $R^{13}$ are independently selected from H, alkyl, cycloalkyl, cycloalkenyl, heterocycloalkyl, alkenyl, alkynyl, aralkyl, aryl and heteroaryl;

or $R^{12}$ and $R^{13}$ may be taken together with the nitrogen to which they are attached form a 5- to 7-membered ring which may optionally contain a further heteroatom;

a is 0 to 6;

b is 0 to 6;

$R^3$ is selected from the group consisting of halo, alkyl, CN, $NO_2$, $CO_2R^{31}$, $C(O)R^{31}$, —O—$R^{31}$, —$N(R^{32})(R^{33})$, —$N(R^{31})C(O)R^{31}$, —$N(R^{31})SO_2R^{31}$, —$SR^{31}$, —C(O)N$(R^{32})(R^{33})$, —$OC(O)R^{31}$, —$OC(O)N(R^{32})(R^{33})$, $SO_2$, —$SOR^{31}$, —$SO_3R^{31}$, —$SO_2N(R^{32})(R^{33})$, cycloalkyl, cycloalkenyl, heterocycloalkyl, aralkyl, aryl and heteroaryl, each $R^{31}$ is independently selected from H, alkyl, cycloalkyl, cycloalkenyl, alkenyl, alkynyl, aralkyl, aryl and heteroaryl;

$R^{32}$ and $R^{33}$ are independently selected from H, alkyl, cycloalkyl, cycloalkenyl, heterocycloalkyl, alkenyl, alkynyl, aralkyl, aryl and heteroaryl;

or $R^{32}$ and $R^{33}$ may be taken together with the nitrogen to which they are attached form a 5- to 7-membered ring which may optionally contain a further heteroatom; or $R^3$ is a group of the formula

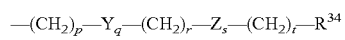

wherein Y and Z are independently selected from O, S, —OCH$_2$CH$_2$O—, —C(R$^{36}$)$_2$C(O)—

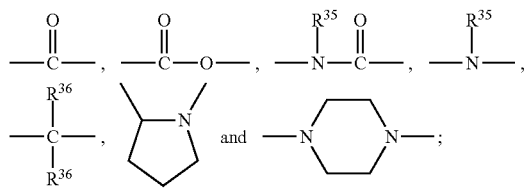

p, r and t are independently selected from values from 0 to 10;
q and s are independently selected from 0 and 1, provided that when t=0 then s=0,
and when r=0 then q=0; and
R$^{34}$ is selected from OR$^{35}$, CO$_2$R$^{35}$, —NH—CO$_2$R$^{35}$, —NHC(O)—CH$_2$OR$^{35}$ and

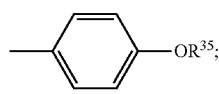

each R$^{35}$ is independently selected from the group consisting of H, alkyl, alkenyl, alkynyl, cycloalkyl, heterocycloalkyl, aralkyl, aryl and heteroaryl;
each R$^{36}$ is independently selected from the group consisting of H, alkyl, alkenyl, alkynyl, cycloalkyl, heterocycloalkyl aralkyl, aryl, heteroaryl; CO$_2$R$^{37}$, C(O)R$^{37}$, —O—R$^{37}$, —N(R$^{37}$)(R$^{37}$), —N(R$^{37}$)C(O)R$^{37}$, —N(R$^{37}$)SO$_2$R$^{37}$, —C(O)N(R$^{37}$)(R$^{37}$), —OC(O)R$^{37}$, and —OC(O)N(R$^{37}$)(R$^{37}$);
R$^{37}$ is selected from H, alkyl, alkenyl, alkynyl, cycloalkyl, heterocycloalkyl, aralkyl, aryl and heteroaryl
n is selected from 0-4, and
m is 0 or 1, with the proviso that the sum of n plus m does not exceed 4;
R$^4$ is selected from the group consisting of alkyl, cycloalkyl, heterocycloalkyl, alkenyl, alkynyl, aralkyl, aryl, heteroaryl, —(CH$_2$)$_e$C(O)(CH$_2$)$_f$R$^{41}$, —(CH$_2$)$_e$C(O)N(R$^{42}$)(R$^{43}$), —(CH$_2$)$_e$C(O)O(CH$_2$)$_f$R$^{41}$, —(CH$_2$)$_e$C(O)N(R$^{42}$)(R$^{43}$), and —(CH$_2$)$_e$N(R$^{42}$)(R$^{43}$),
each R$^{41}$ is independently selected from H, alkyl, cycloalkyl, cycloalkenyl, heterocycloalkyl, alkenyl, alkynyl, aralkyl, aryl and heteroaryl;
R$^{42}$ and R$^{43}$ are independently selected from H, alkyl, cycloalkyl, cycloalkenyl, heterocycloalkyl, alkenyl, alkynyl, aralkyl, aryl and heteroaryl;
or R$^{42}$ and R$^{43}$ may be taken together with the nitrogen to which they are attached form a 5- to 7-membered ring which may optionally contain a further heteroatom;
e is 1 to 6;
f is 1 to 6; and
R$^5$ is selected from H and an alcohol protecting group.

In a preferred embodiment of the invention, R$^1$ and R$^4$ are selected to be the same for compounds of the formula III.

The compounds of the III are useful as intermediates in the preparation of the compounds of the formula I and II. In other embodiments, the compounds of the formula III may be used as the active compound in a pharmaceutical preparation. In this embodiment, the compound of the formula III may be present in the pharmaceutical preparation as a pharmaceutically acceptable salt or hydrate.

The compounds according to the invention may also be present as salts. In the context of the invention, preference is given to pharmaceutically acceptable salts. Pharmaceutically acceptable salts refers to an acid addition salt or a basic addition salt of a compound of the invention in which the resulting counter ion is understood in the art to be generally acceptable for pharmaceutical uses. Pharmaceutically acceptable salts can be salts of the compounds according to the invention with inorganic or organic acids. Preference is given to salts with inorganic acids, such as, for example, hydrochloric acid, hydrobromic acid, phosphoric acid or sulfuric acid, or to salts with organic carboxylic or sulfonic acids, such as, for example, acetic acid, maleic acid, fumaric acid, malic acid, citric acid, tartaric acid, lactic acid, benzoic acid, or methanesulfonic acid, ethanesulfonic acid, phenylsulfonic acid, toluenesulfonic acid or naphthalenedisulfonic acid. Pharmaceutically acceptable salts can also be metal or ammonium salts of the compounds according to the invention. Particular preference is given to, for example, sodium, potassium, magnesium or calcium salts, and also to ammonium salts which are derived from ammonia or organic amines, such as, for example, ethylamine, di- or triethylamine, di- or triethanolamine, dicyclohexylamine, dimethylaminoethanol, arginine, lysine, ethylenediamine or 2-phenylethylamine. (see, Berge et al. *J. Pharm. Sci.* 1977, 66, 1-19).

When one or more chiral centers are present in the compounds of the present invention, the individual isomers and mixtures thereof (e.g., racemates, etc.) are intended to be encompassed by the formulae depicted herein. In certain embodiments, compounds of the invention may exist in several tautomeric forms. Accordingly, the chemical structures depicted herein encompass all possible tautomeric forms of the illustrated compounds. Compounds of the invention may exist in various hydrated forms.

It is understood that when n is a value greater than 1, each R$^1$ group may be selected independently. Thus, when more than one R$^1$ group is present, the R$^1$ groups may be selected from any of the stated groups so as to be the same or different. This also holds true for any other group or substituent which may be selected independently from among various groups or values.

In another aspect of the invention, a synthetic process for the preparation of compounds of the invention is provided. The inventive process uses mild reaction conditions, which provides a high substituent tolerance. The product is obtained in high yield and high purity.

The benzofuran derivatives of the present invention may be prepared using a process of carbonylative annulation as shown in Scheme 1:

Scheme 1

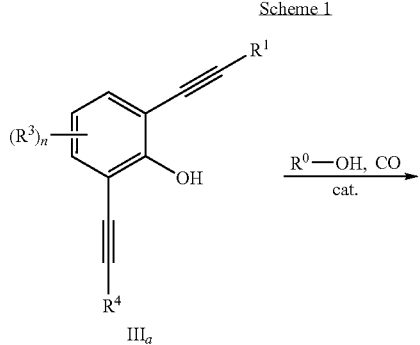

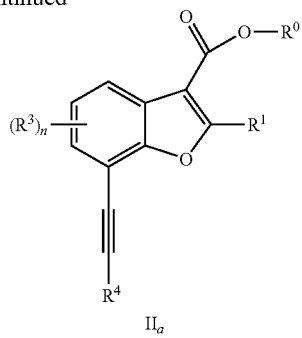

IIa

A compound of the formula III$_a$ is treated with an alcohol of the formula R$^0$—OH in the presence of a transition metal catalyst, carbon monoxide and a base, wherein R$^1$, R$^3$, R$^4$, and n are as described above for the compound of the formula I, and R$^0$ is a protecting group or is R$^{21}$. Examples of useful conditions for the carbonylative annulation may be found in Hu, Y.; Zhang, Y.; Yang, Z. and Fathi, R., *J. Org. Chem.* 2002, 67, 2365-2368; Hu, Y.; Nawoschik, K.; Liao, Y.; Ma, J.; Fathi, R. and Yang, Z., *J. Org. Chem.* 2004, 69, 2235-2239; Liao, Y.; Reitman, M.; Zhang, Y.; Fathi, R. and Yang, Z., *Organic Letters* 2002, 4(5), 2607-2609.

The transition metal catalyst is preferably a palladium(II) compound, such as Pd(PPh$_3$)$_2$Cl$_2$, Pd(PPh$_3$)$_4$, Pd(OAc)$_2$, PdCl$_2$, PdI$_2$, PdI$_2$-thiourea, Pd(CH$_3$CN)$_2$Cl$_2$, and Pd(bpy)Cl$_2$. A particularly preferred catalyst is Pd(PPh$_3$)$_2$Cl$_2$ in the presence of a ligand such as dppp, 2,2'-dipyridyl (bpy), 2-PyPPh$_2$, thiourea, CBr$_4$, and p-methylphenylsulfonyl. Preferred bases include, but are not limited to, metal salts, such as alkali metal acetates, carbonates, and phosphates. A particularly preferred base in CsOAc. Suitable organic solvents include THF, CH$_3$CN, benzene, toluene, dioxane and polar aprotic solvents such as DMF. A particularly preferred solvent is DMF. The carbonylative annulation preferably is performed at a temperature of about 45° C. to about 100° C.

The ester product (II$_a$) undergoes further chemical modification. In one embodiment, the ester group is cleaved by saponification or other method known in the art to give the corresponding carboxylic acid, (for a review of ester cleavage reactions see Greene, T. W.; Wuts, P. G. M. *Protective Groups in Organic Synthesis*, 2$^{nd}$ ed.; (Wiley: New York, 1991), pages 229-270, particularly pages 229-231, and the references contained therein). As would be apparent to a person of ordinary skill in the art, the method for cleavage of the ester should be compatible with the other substituents and with the solid support and linker (for a solid phase synthesis). The resulting carboxylic acid, can be activated for further reaction by a method known in the art, for example, as an acid halide or anhydride, or through the use of dehydrating agents, such as DCC. Alternatively, an active ester may be introduced directly into the compound of the formula II$_a$ by selection of an appropriate alcohol, R$^0$—OH, for use in the carbonylative annulation. A preferred active ester is derived from the alcohol HO—CH$_2$—CF$_3$ (R$^0$=CH$_2$—CF$_3$). The term "active ester" as used herein contemplates esters that are readily susceptible to nucleophillic substitution, for example, by transesterification. Thus, in another embodiment of the invention, the ester II$_a$ may be treated with a base followed by conversion into another chemical group (for example, the amide is shown below).

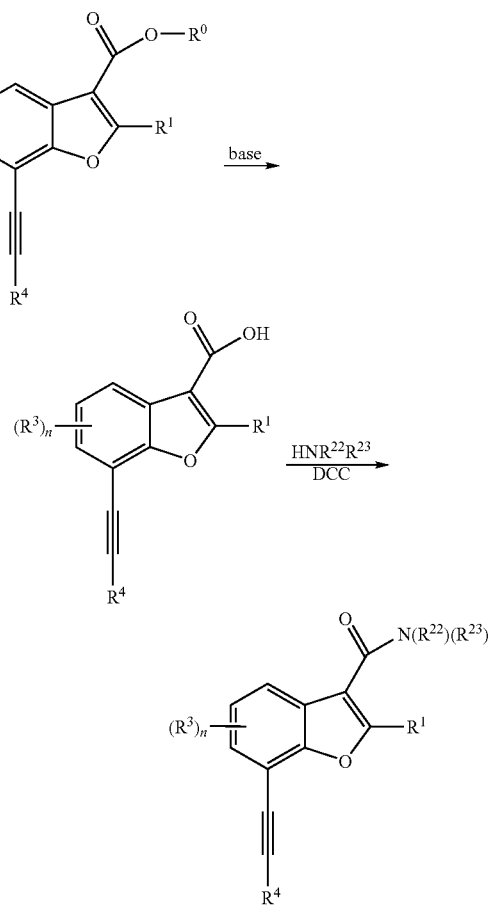

Compounds of the formula III may be prepared using the Sonogashira reaction. In the preferred embodiment where R$^1$ is the same as R$^4$, Scheme 2 may be used:

Scheme 2

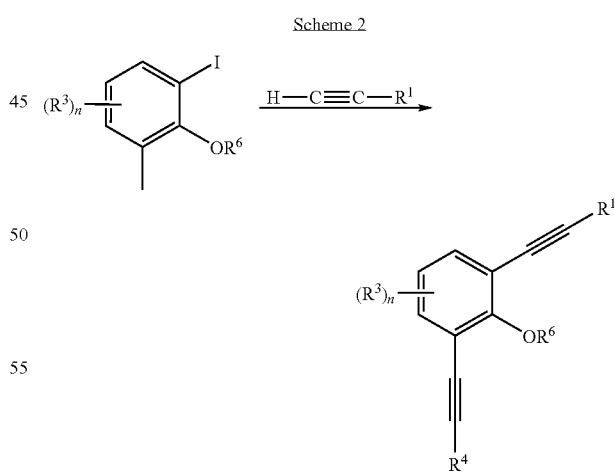

Using the Sonogashira reaction, an aryl iodide is treated with a terminal alkyne in the presence of base and a transition metal catalyst. R$^6$ represents an alcohol protecting group, and may be, for example, an ester of other protecting group as would be apparent to the ordinarily skilled practitioner (for a discussion of suitable protection groups, see Greene, T. W.; Wuts, P. G. M. *Protective Groups in Organic Synthesis*, 2$^{nd}$ ed.; Wiley: New York, 1991). A suitable base may be, for example, an organic base such as a primary, secondary or tertiary amine. Non-limiting examples include triethylamine, diisopropylamine, 1,8-diazabicyclo-[5.4.0]-undec-7-ene (DBU), 1,5-diazabicyclo-[4,3,0]-non-5-ene (DBN), or 1,4-diazabicyclo-[2.2.2]-octane (DABCO). Alternatively, an inorganic base may be used, such as an alkali metal or alkaline earth metal salt, such as a carbonate, bicarbonate or acetate salt.

The metal catalyst may be in the form of a salt or a complex with organic ligands. Particularly suitable metal catalysts are, for example, the Group VIII metals, preferably Pd(0) complexes or a Pd(II) salt. The ligands may be selected from, for example, phosphorus-containing ligands, such as triphenylphosphine (PPh$_3$) and 1,2-bis(diphenyl-phosphino) ethane (dppe). Preferred palladium catalysts include Pd(PPh$_3$)$_2$Cl$_2$, Pd(PPh$_3$)$_4$ and Pd(OAc)$_2$. The reaction is performed in the presence of a Cu(I) salt, such as a Cu(I) halide, Cu$_2$O, and CuCN, preferably CuI or CuCl. Suitable organic solvents include, but are not limited to, dioxane, tetrahydrofuran (THF) dimethylformamide (DMF), acetonitrile, dimethylsulfoxide, and other polar aprotic solvents or mixtures thereof. For further discussion of the Sonogashira reaction, see Sonogashira, K.; Tohda, Y.; Hagihara, N. *Tetrahedron Lett.* 1975, 4467-4470; Sonogashira, K. In *Comprehensive Organic Synthesis, Trost, B. M.; Fleming, L., Eds., Pergamon Press: New York,* 1991, Vol. 3, chapter 2.4; Liao, Y.; Fathi, R.; Reitman, M.; Zhang, Y.; Yang, Z. *Tetrahedron Lett.* 2001, 42, 1815-1818; Nicolaou, K. C.; Smith, A. L. *Acc. Chem. Res.* 1992, 25, 497-503; Porco, J. A., Jr.; Schoenen, F. J.; Stout, T. J.; Clardy, J.; Schreiber, S. L. *J. Am. Chem. Soc.* 1990, 112, 7410-7411; Hundertmark, T.; Littke, A. F.; Buchwald, S. L.; Fu, G. C. *Org. Lett.* 2000, 2, 1729-1731, and references therein; Takeuchi, R.; Tanabe, K.; Tanaka, S. *J. Org. Chem.* 2000, 65, 1558-1561; Arterburn, J. B.; Rao, K. V.; Perry, M. C. *Tetrahedron Lett.* 2000, 41, 839-842; Gan, Z.; Roy, R. *Tetrahedron Lett.* 2000, 41, 1155-1159; Godt, A.; Unsal, O.; Roos, M. *J. Org. Chem.* 2000, 65, 2837-2842; Wu, M. J.; Lin, C. F.; Chen, S. H. *Org. Lett.* 1999, 1, 767-768; Yoshimura, F.; Kawata, S.; Hirama, M. *Tetrahedron Lett.* 1999, 40, 8281-8286; Ma, S.; Shi, Z.; Yu, Z. *Tetrahedron Lett.* 1999, 40, 2393-2396; Tretyakov, E. V.; Knight, D. W.; Vasilevsky, S. F. *J. Chem. Soc., Perkin Trans.* 1, 1999, 3713-3720; Thorand, S.; Krause, N. *J. Org. Chem.* 1998, 63, 8551-8553; and Sonogashira, K. in *Metal-Catalyzed Cross-Coupling Reactions*; Diederich, F., Stang, P. J., Wiley-VCH: New York, 1998; Chapter 5, each of which is incorporated by reference.

In one embodiment, the process of the invention is adapted for use as a solid phase synthesis. In a solid phase synthesis the reactions are carried out on macroscopic particles (as known as the solid support, or resin) made of material that is insoluble in the reaction mixture, to which one of the reactants is bound. In preferred embodiments, a functional group (such as —OH, —NH$_2$, CO$_2$H, C(O)NH$_2$, etc.) on R$^3$ is employed to bind an intermediate to the solid phase. In further embodiments, an R$^3$ group is bound to the solid phase through a linker.

The solid support is an insoluble, functionalized, polymeric material to which library members or reagents may be attached via a linker, allowing them to be readily separated (by filtration, centrifugation, etc.) from excess reagents, soluble reaction by-products, or solvents. The solid support is chosen from the solid support materials known in the art, e.g., commercially available resins used for solid phase synthesis in combinatorial chemistry or in solid phase peptide synthesis. For example, the solid support may be chosen from cross-linked polystyrene resins, polystyrene/DVB-polyethylene resins (for example, TentaGel resin, ArgoGel, etc.), controlled-pore glass and Kieselguhr/polyacrylamide. A preferred solid support is a high-capacity polystyrene macrobead.

The linker is a chemical moiety that provides a means of attachment for the immobilized chemical reagent to the solid support. The linker may be any chemical component capable of being selectively cleaved to release the product from the solid support. Yields for the loading and cleavage to the linker should be as quantitative as possible. The linker may be chosen from those customarily used in the art that are stable to the reactions conditions. Examples of suitable linkers may be found in the review by Guillier et al., *Chem. Rev.* 2000, 100, 2019-2157. Preferred linkers are silyl based linkers, for example the silyl based linkers disclosed in Sternson et al., *J. Am. Chem. Soc.* 2001, 123, 1740-1747, Blackwell et al., *Org. Lett.* 2001, 3, 1185-1188, Pelish et al., *J. Am. Chem. Soc.* 2001, 123, 6740-6741, and Tallarico et al., *J. Comb. Chem.* 2001, 3, 312-318, and the like.

It may be advantageous to employ a temporary protecting group in achieving the final product. The phrase "protecting group" as used herein means temporary modifications of a potentially reactive functional group which protect it from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis,* 2$^{nd}$ ed.; Wiley: New York, 1991).

The compounds and processes disclosed herein are useful in the production of a library of benzofuran derivatives for biological screening. Derivatives of benzofuran posses a range of biological activities. Benzofuran-based compounds have shown efficacy, for example, as antivirals. Particularly, the compounds of the present invention may be used to prevent or treat infection with HCV.

The identification of inhibitors of HCV replication and/or proliferation has been facilitated by the development of a cell based system to study HCV replication and assay for HCV inhibitors. Inhibition of HCV replication may be performed using the HCV Replicon Assay developed in the laboratories of Bartenschlager (Lohman et al, *Science* 285, 110-113, 1999) and Rice (Blight et al, *Science* 290, 1972-1974, 2000). The assay is performed using the Huh-Luc-Neo cell line (Lohman et al, *Science* 285, 110-113, 1999). Huh-Luc-Neo cells are a human hepatoma cell line (Huh-7) stably expressing a bi-cistronic subgenomic replicon containing the HCV IRES in which the structural proteins of HCV had been deleted and replaced by a construct containing sequences coding for the firefly luciferase reporter gene, the neomycin selectable marker and the EMCV IRES to direct expression of a truncated HCV genome expressing the structural proteins NS3, NS4A, NS4B, NS5A, and NS5B. HCV targets through which inhibitors could act to inhibit replication include the NS3 protease, the helicase/ATPase, NS5A, the NS5B-RNA dependent RNA polymerase, and the HCV IRES.

Expression of HCV IRES driven luciferase reporter activity and HCV RNA is measured to obtain indirect and direct measures of replication of HCV RNA respectively. Inhibitors of HCV replication and/or proliferation are determined by initially identifying molecules that inhibit expression of the HCV IRES driven luciferase reporter in this HCV Replicon Luciferase Assay. Cell viability assays and control cell based luciferase assays are then run on hits identified in the HCV Replicon Luciferase Assay to eliminate cytoxic compounds and non-specific compounds which act by inhibiting the luciferase enzyme. Validated inhibitors of HCV replication and/or proliferation are identified by evaluating HCV Replicon Luciferase hits that are specific and non-cytoxic and demonstrating that these compounds inhibit expression of HCV RNA using a quantitative PCR based approach (Taqman) using primers and probes specific for HCV RNA (HCV Replicon RNA Assay).

The HCV Replicon Assay may be used to predict compound efficacy in treatment and/or prevention of HCV infection as well as inhibition of HCV replication and/or proliferation. The HCV Replicon encompasses a multiplicity of viral and host targets through which an inhibitor could work to inhibit HCV Replication. Viral targets expressed in the HCV Replicon include the HCV IRES (for translation), NS3 Protease, the HCV Helicase/ATPase, NS5A phosphorylation, and the NS5B polymerase. Without being limited to theory, it is believed that the compounds of the present invention inhibit HCV replication. The compounds of the invention may inhibit replication as by acting on the IRES, NS3 protease, NS5B polymerase, Helicase/ATPase, or NS5A phosphorylation.

Thus, in another embodiment, the present invention provides pharmaceutical compositions comprising an anti-HCV effective amount of a compound of formula I, or a pharmaceutically acceptable salt or hydrate thereof, in combination with a pharmaceutically acceptable carrier or auxiliary agent. As used herein, the terms "pharmaceutically acceptable salts" and "hydrates" refer to those salts and hydrated forms of the compound that would favorably affect the physical or pharmacokinetic properties of the compound, such as solubility, palatability, absorption, distribution, metabolism and excretion. Other factors, more practical in nature, which those skilled in the art may take into account in the selection include the cost of the raw materials, ease of crystallization, yield, stability, solubility, hygroscopicity and flowability of the resulting bulk drug.

The invention also provides a method of treating HCV infection in a mammal, preferable a human, by administering to the mammal an effective amount of a compound of the present invention, a pharmaceutically acceptable salt or hydrate thereof, or a composition as described above. The compounds of the invention may be administered alone or may be administered in combination with other approved therapeutics, such as: an interferon (pegylated or not), preferably α-interferon, ribavirin, or interferon and ribavirin, or one or more other anti-HCV agent, such as an HCV protease inhibitor, HCV polymerase inhibitor, HCV IRES inhibitor, HCV Helicase and/or ATPase inhibitor, NS5A phosphorylation inhibitor, HCV NS2 inhibitor, or other HCV life cycle inhibitor. Combination therapies with may include a compound of the invention with multiple different inhibitors of HCV life cycle (immunomodulatory agents, Toll Like Receptor modulators, antisense therapeutics etc.). The agents that comprise a combination therapy may be administered together or separately, e.g., prior to, concurrently with or following the administration of the compound of the invention or pharmaceutically acceptable salt thereof. These additional agents may be combined with the compounds of this invention to create a single pharmaceutical dosage form. Alternatively these additional agents may be separately administered to the patient as part of a multiple dosage form, for example, using a kit. Such additional agents may be administered to the patient prior to, concurrently with, or following the administration of wherein a compound of formula (I), or a pharmaceutically acceptable salt thereof.

The compounds of the present invention may be employed in solid or liquid form including, for example, amorphous powder or crystalline form, in solution or in suspension. They may be administered in numerous different ways, such as orally, parenterally, topically, transdermally or by inhalation. Oral administration or administration by injection is preferred. The choice of carrier and the content of active compound in the carrier are generally determined in accordance with the solubility and chemical properties of the desired product, the particular mode of administration and well established pharmaceutical practice. The pharmaceutical composition of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intra-articular, intrasynovial, intrasternal, intrathecal, and intralesional injection or infusion techniques.

Examples of liquid carriers include syrups, peanut oil, olive oil, water, saline and the like. For parenteral administration, emulsions, suspensions or solutions of the compounds according to the invention in vegetable oil, for example sesame oil, groundnut oil or olive oil, or aqueous-organic solutions such as water and propylene glycol, injectable organic esters such as ethyl oleate, as well as sterile aqueous solutions of the pharmaceutically acceptable salts, may be used. Injectable forms must be fluid to the extent they can be easily syringed, and proper fluidity can be maintained, for example, by the use of a coating such as lecithin, by the maintenance of the required particle size in the case of dispersion and by the use of surfactants. Prolonged absorption of the injectable compositions can be brought about by use of agents delaying absorption, for example, aluminum monostearate and gelatin. The pharmaceutical composition may be in the form of a sterile injectable preparation, for example, as a sterile injectable aqueous or oleaginous suspension. This suspension may be formulated according to techniques known in the art using suitable dispersing or wetting agents (such as, for example Tween 80) and suspending agents.

The pharmaceutical composition of this invention may be orally administered in any orally acceptable dosage form including, but not limited to, capsules, tablets, and aqueous suspensions and solutions. Compounds of the invention may be enclosed in hard or soft shell gelatin capsules, or compressed into tablets. Examples of oral liquid dosage forms include solutions, suspensions, syrups, emulsions, soft gelatin capsules and the like. Carriers for oral use (solid or liquid) may include time delay materials known in the art, such as glyceryl monostearate or glyceryl distearate alone or with a wax. To prepare a capsule, it may be advantageous to use lactose and a liquid carrier, such as high molecular weight polyethylene glycols.

Compositions and dosage forms prepared in accordance with the present invention optionally may contain lactose, sodium citrate, calcium carbonate, dicalcium phosphate and disintegrating agents such as starch, alginic acids and certain complex silica gels combined with lubricants such as magnesium stearate, sodium lauryl sulfate and talc may be used for preparing tablets, capsules and the like. Various other materials may be present as coatings or to otherwise modify the physical form of the dosage unit. For instance, tablets, and capsules may be coated with shellac, sugar or both. When aqueous suspensions are used they may contain emulsifying agents or agents which facilitate suspension. Diluents such as sucrose, ethanol, polyols such as polyethylene glycol, propylene glycol and glycerol, and mixtures thereof also may be used. In addition, the active compound may be incorporated into sustained-release preparations and formulations. If desired, certain sweetening and/or flavoring and/or coloring agents may be added. Other suitable vehicles or carriers for the above noted formulations and compositions can be found in standard pharmaceutical texts, e.g. in "Remington's Pharmaceutical Sciences", The Science and Practice of Pharmacy, 19.sup.th Ed. Mack Publishing Company, Easton, Pa., (1995).

When these compounds or their pharmaceutically acceptable salts are formulated together with a pharmaceutically acceptable carrier, the resulting composition may be administered in vivo to mammals, such as man, to treat or prevent HCV virus infection. Such treatment may also be achieved using a compound of this invention in combination with other anti-viral agents which include, but are not limited to a-interferon and ribavirin. The additional agents may be combined with compounds of this invention to create a single dosage form. Alternatively these additional agents may be separately administered to a mammal as part of a multiple dosage form.

EXAMPLES

General Methods

Reaction solvents were commercially purchased from Acros and Aldrich without further purification and reagents were used as received. Reactions for the synthesis of the starting material were monitored by thin-layer chromatography (TLC) on 0.25 mm precoated Merck Silica Gel 60 $F_{254}$, visualizing with ultraviolet light or phosphomolybdic acid stain. Flash column chromatography was performed on Merck Silica Gel 60 (230-400 mesh) using reagent grade hexanes, dichloromethane, methanol and ethyl acetate.

Solid Phase Reactions:

Reaction Apparatus: Small-scale solid phase reactions (1-20 mg resin) were performed in 1 or 2 mL of polypropylene Fisherbrand® flat top microcentrifuge tubes (Fisher Scientific 05-408-25A) or 1 or 2 mL of fritted polypropylene Bio-Spine® chromatography columns (Bio-Ras 732-6008) with 360° rotation on a Barnstead-Thermilyne Labquake™ Shaker (VWR 56264-306) or a Genie 2™ Fisher Vortex (cat. 12-812).

Standard Washing Procedure: The washing was carried out on a Vac-Man® Laboratory Vacuum Manifold (Promega A7231) with 2-way Teflon stopcocks. The following standard wash procedure was used in sequence: $CH_2Cl_2$, DMF, MeOH, DMF, $CH_2Cl_2$ (each for 1-2 h).

Standard Cleavage and drying procedure: The resins (10 beads) were suspended in THF (0.2 mL), then HF/Pyridine (0.01 mL) was added. The mixture was shaken for 1 h, then methoxytrimethylsilane ((trimetylsilyl)methanol) (TMSOMe) (0.02 mL) was added and the mixture was further shaken for another 5 min. Most solvents and reagents were removed in a GeneVac VC3000D vapour condenser (IP-SWICH England) for 30 min and further dried in Dura-Dry™ Freeze-dryer at <50 mT for 1-3 days.

Analysis: All LC-MS spectra were obtained on a Micromass ZQ mass spectrometer in electrospray positive ionization (ES+) mode in line with a Waters 2790 HPLC system (Separations Module, Alliance™). LC-MS chromatography was performed on a Waters Symmetry C18 Column (3.5 μm, 2.1×50 mm, W93491F 26) using a flow rate of 0.4 mL/min in a gradient of 15-100% $CH_3CN$ in $H_2O$ in 9 min with 1 min wash. Column temperature: 30° C. [ES$^+$]: Capillary (kV): 3.5; Cone (V): 70; Extractor (V): 5; RF Lens (V): 0.3; Source temperature (° C.): 150; Cone temperature (° C.): 20; Desolvation temperature (° C.): 400; Cone gas flow (L/Hr): 114; Desolvation gas flow (L/Hr): 466. Injection Volume: 10 μl. Software: Masslynx. Normally, product cleaved from one bead is sufficient for LC-MS analysis. After the product was dried completely, it was dissolved in 0.15 mL THF (HPLC grade) for LC-MS test, which was reported as: LC-MS (retention time, [M+1]$^+$./[M+Na]$^+$.(ES+)).

Example 1

Carbonylative Annulation (General Stoichiometric Method)

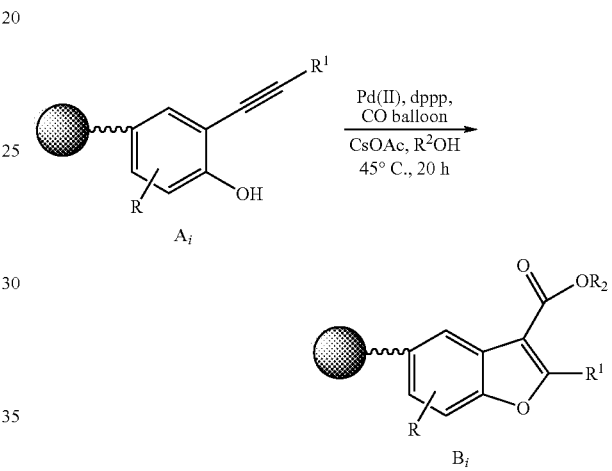

To proceed with carbonylative annulation reaction, each portion of the deprotected beads $A_i$ (10 mg) was treated with Pd(PPh$_3$)$_2$Cl$_2$ (9.1 mg, 0.013 mmol, 1.1 equiv), dppp (5.4 mg, 0.013 mmol, 1.1 equiv) and CsOAc (46 mg, 0.24 mmol, 20 equiv), which were mixed and degassed under high vacuum with CO 3 times followed by addition of the dry DMF (1 mL) and R$^2$OH (20 equiv); The mixtures were then stirred at 45° C. under balloon pressure of CO. After 20 hrs, the mixtures were filtered and washed extensively (see *Standard Washing Procedure*) to generate $B_i$, which was cleaved from the beads and dried (see *Standard Cleavage and drying Procedure*).

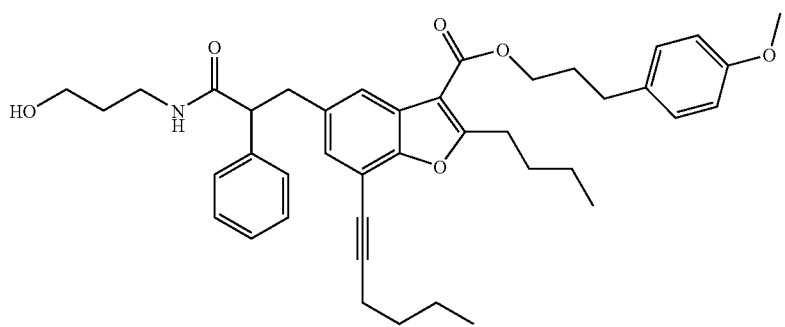

VQ_22258
LC-MS: 7.05 min, [M + 1]$^+$· 652 (ES+).

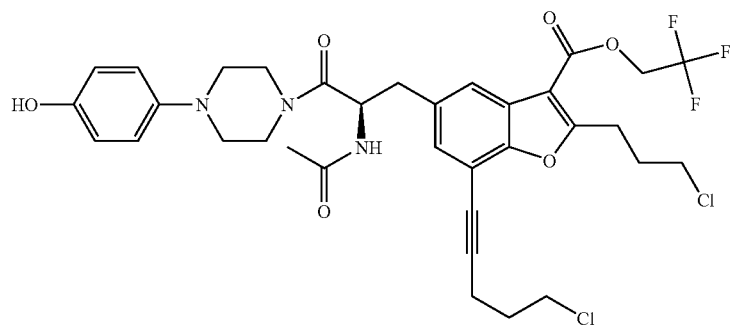
VQ_22288
LC-MS: 5.01 min, [M + Na]+ 732 (ES+).
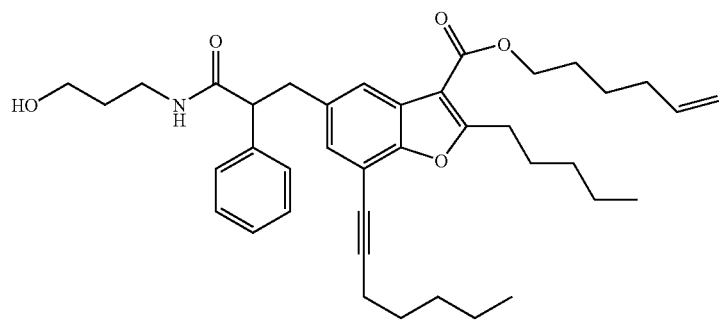
VQ_22237
LC-MS: 7.31 min, [M + Na]+ 636 (ES+).
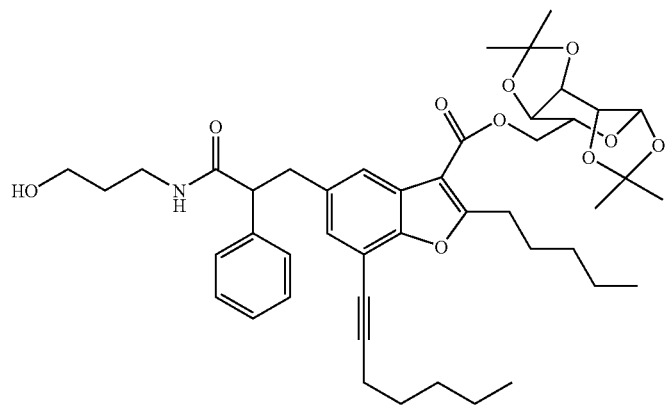
VQ_22243
LC-MS: 6.94 min, [M + Na]+ 796 (ES+).
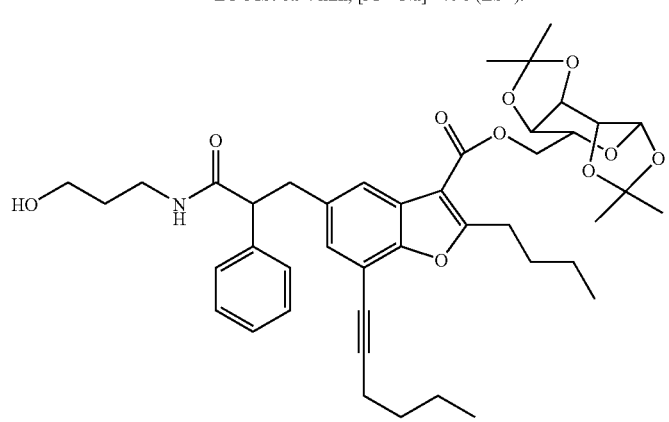
VQ_22266
LC-MS: 6.74 min, [M + Na]+ 768 (ES+).

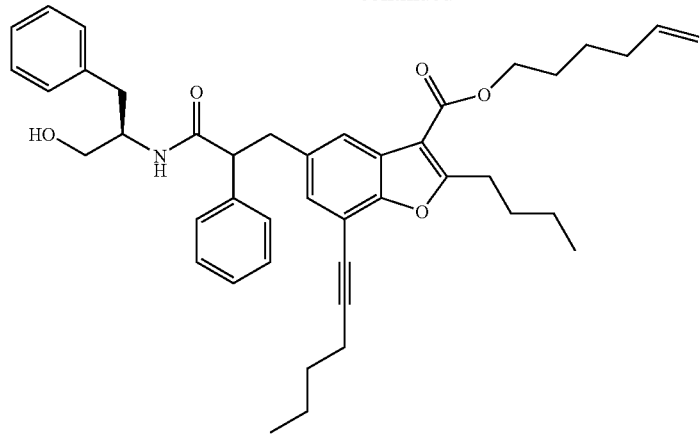

VQ_35983
LC-MS: 7.04 min, [M + 1]$^{+\cdot}$ 587 (ES+).

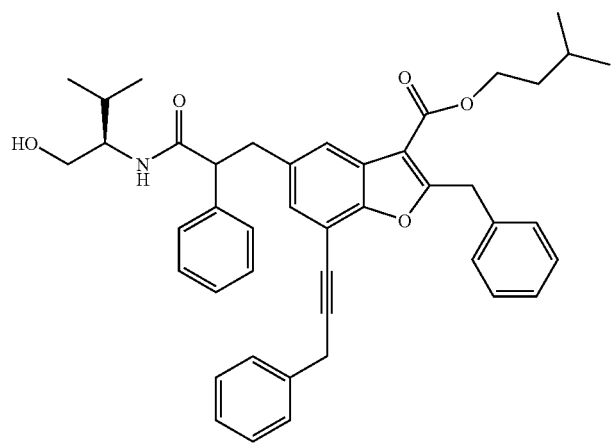

VQ_35759
LC-MS: 6.91 min, [M + 1]$^{+\cdot}$ 670 (ES+).

Example 2

HCV Replicon Luciferase Assay

Day 0, Cell Seeding and Compound Treatment: Huh-Luc-Neo Cells are seeded at 25,000/well in an opaque-walled 96 plate with Growth Medium (DMEM phenol red free+PS+2 mM glutamine; 100 μl/well). The compounds to be tested are added to the experimental wells (10 μl/well at 10× assay concentration) and the cells are then incubated (5% $CO_2$, 37° C.) for 48 h.

Day 2, Reagent Preparation and Luciferase Assay: The Bright-Glo Luciferase Assay Buffer (Promega) is thawed and equilibrated to room temperature prior to use. The lyophilized Bright-Glo Luciferase Assay Substrate is equilibrated to room temperature prior to use. 10 ml of Bright-Glo Luciferase Assay Buffer is transferred to 1 vial of Bright-Glo Luciferase Assay Substrate bottle and mixed by gently with a Vortex. 100 ul of Bright-Glo Luciferase Assay reagent (Bright-Glo Luciferase Assay Buffer+Bright-Glo Luciferase Assay Substrate Mixture) is added to each well. The well contents are mixed for 5 min. on an orbital shaker at room temperature to induce cell lysis and the luminescence is then measured using a luminometer. The data is analyzed and IC50s are determined using GraphPad Prism 4 software. Hits validated in the Replicon Luciferase assay have IC50s<8.0 μM and show <30% inhibition of Cell Viability at a compound concentration of 100 μM (Cell Titer Glow Assay, cell viability assay conditions identical to HCV Replicon Luciferase Assay conditions).

Example 3

HCV Replicon RNA Assay

Day 0, Cell Seeding and Compound Treatment: Huh-Luc-Neo Cells are seeded at 25,000/well in an opaque-walled 96 plate with Growth Medium (DMEM phenol red free+PS+2 mM glutamine; 100 μl/well). The compounds to be tested are added to the experimental wells (10 μl/well at 10× assay concentration) and the cells are then incubated (5% $CO_2$, 37° C.).

Day 1, Media Change and Compound Treatment: 24 hours after the initial compound treatment the cell culture media is aspirated from the wells and fresh Growth Medium is added (DMEM phenol red free+PS+2 mM glutamine; 100 μl/well). The compounds to be tested are then added to the appropriate experimental wells (10 μl/well at 10× assay concentration) and the cells are then incubated (5% CO2, 37° C.) for an additional 24 hrs.

Day 2, RNA Isolation and cDNA Synthesis: The cells are washed with 1× Phosphate Buffered Saline (PBS) once. Cells are then lysed and RNA is isolated in 96 well format using a vacuum manifold and the RNAeasy 96 kit (Qiagen) according to the manufacturer's suggested protocol. cDNA is then synthesized from RNA isolated from each well using the Taqman Reverse Transcription Reagents kit (Applied Biosystems) according to manufacturer's suggested protocol.

Day 3, Quantitative PCR Based Measurement of HCV RNA (Taqman Assay): Quantitative PCR analysis to measure HCV RNA expression from cDNA synthesized on Day 2 is performed using the ABI 9700 HT Sequence Detection System (Applied Biosystems) as previously described (Lohman et al, *Science* 285, 110-113, 1999). The data is analyzed and IC50s are determined using GraphPad Prism 4 software. Hits validated in the Replicon RNA Assay have IC50s <8.0 μM and show <30% inhibition of Cell Viability at a compound concentration of 50 μM (Cell Titer Glow Assay, cell viability assay conditions identical to HCV Replicon RNA Assay conditions).

Example 4

CellTiter-Glo Cell Viability Assay (Promega)

Day 0, Cell Seeding and Compound Treatment: Huh-Luc-Neo Cells are seeded at 25,000/well in an opaque-walled 96 plate with Growth Medium (DMEM phenol red free+PS+2 mM glutamine; 100 μl/well). The compounds to be tested for inhibition of cell viability are added to the experimental wells (10 μl/well at 10× assay concentration) and the cells are then incubated (5% $CO_2$, 37° C.) for 48 h.

Day 2, Reagent Preparation and Assay: The CellTiter-Glo Buffer is thawed and equilibrated to room temperature prior to use. The lyophilized CellTiter-Glo Substrate is equilibrated to room temperature prior to use. 10 ml of CellTiter-Glo Buffer is transferred to 1 vial of CellTiter-Glo Substrate and mixed by gently with a Vortex. 100 μl of CellTiter-Glo Assay reagent (CellTiter-Glo Buffer+CellTiter-Glo Substrate Mixture) is added to each well. The well contents are mixed for 5 min. on an orbital shaker at room temperature to induce cell lysis and the luminescence is then measured using a luminometer.

TABLE 2

| Compound | Structure | Luciferase IC50 | Toxicity % Inhibition at 100 uM (1 dose) | TaqMan IC50 | Toxicity % Inhibition at 50uM (2 doses) |
|---|---|---|---|---|---|
| VQ_30668 | 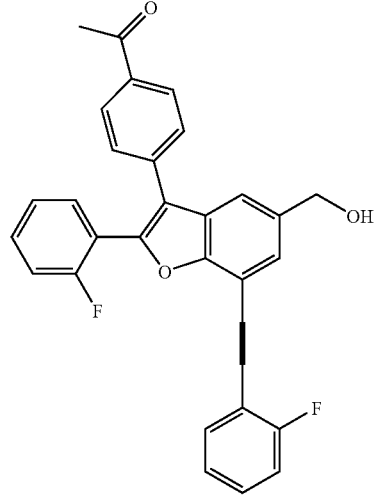 | 2.52 | 26.5 | 0.84 | 7.4 |
| VQ_22266 | 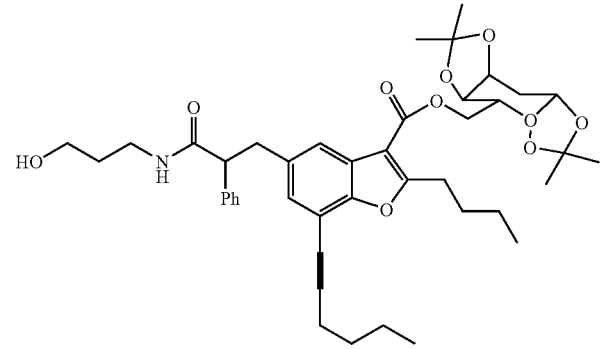 | 2.13 | 27.1 | 1.04 | 8.2 |

TABLE 2-continued
| Compound | Structure | Luciferase IC50 | Toxicity % Inhibition at 100 uM (1 dose) | TaqMan IC50 | Toxicity % Inhibition at 50uM (2 doses) |
|---|---|---|---|---|---|
| VQ_36165 | 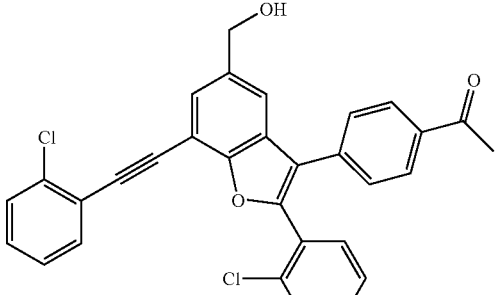 | 5.12 | 10.5 | 1.31 | 5.7 |
| VQ_36167 | 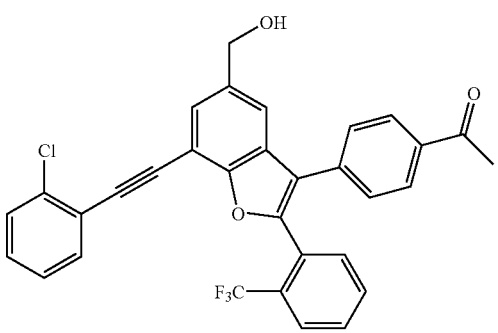 | 12.25 | 33.2 | 1.61 | 20.2 |
| VQ_35983 | 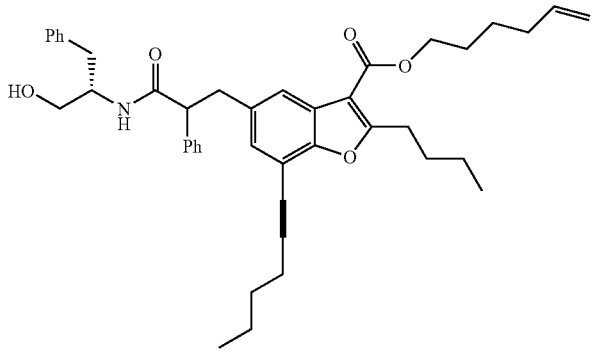 | 10.74 | −3.4 | 1.50 | |
| VQ_35264 | 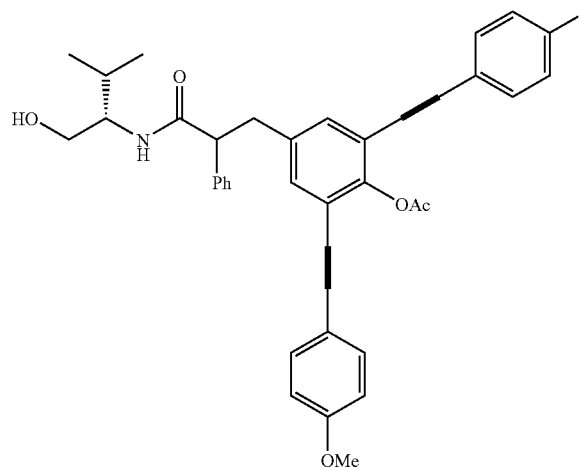 | 0.11 | 6.4 | 0.08 | 19.9 |

TABLE 2-continued

| Compound | Structure | Luciferase IC50 | Toxicity % Inhibition at 100 uM (1 dose) | TaqMan IC50 | Toxicity % Inhibition at 50uM (2 doses) |
|---|---|---|---|---|---|
| VQ_35270 | 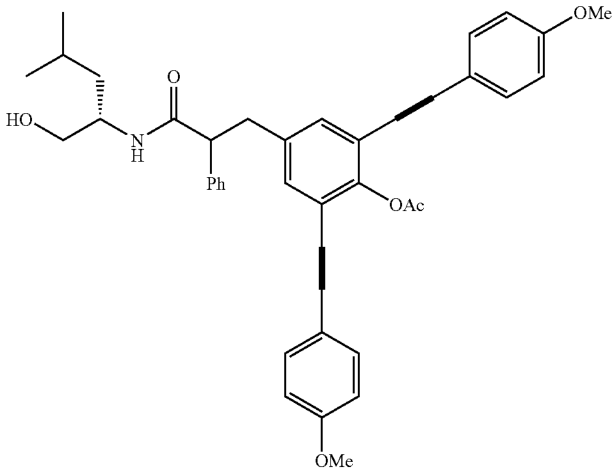 | 0.12 | 20.6 | 0.11 | 28.2 |
| VQ_35284 | 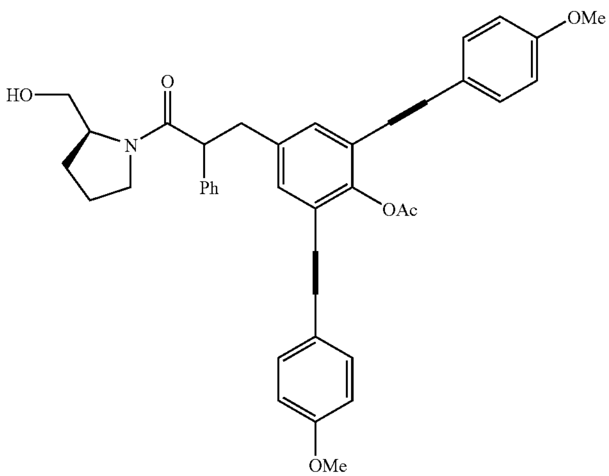 | 0.52 | −13.4 | 0.64 | 9.6 |
| VQ_29705 | 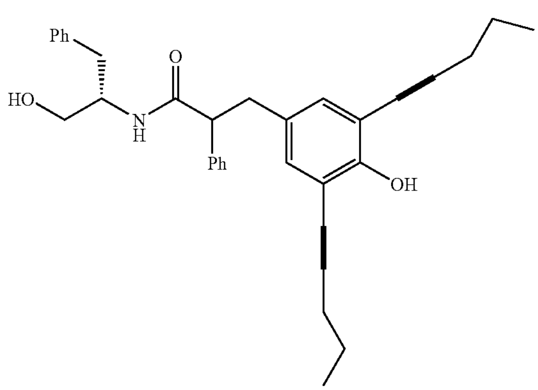 | 6.36 | 1.4 | 2.62 | 25.0 |

What is claimed is:
1. A compound having a structure selected from the group consisting of:
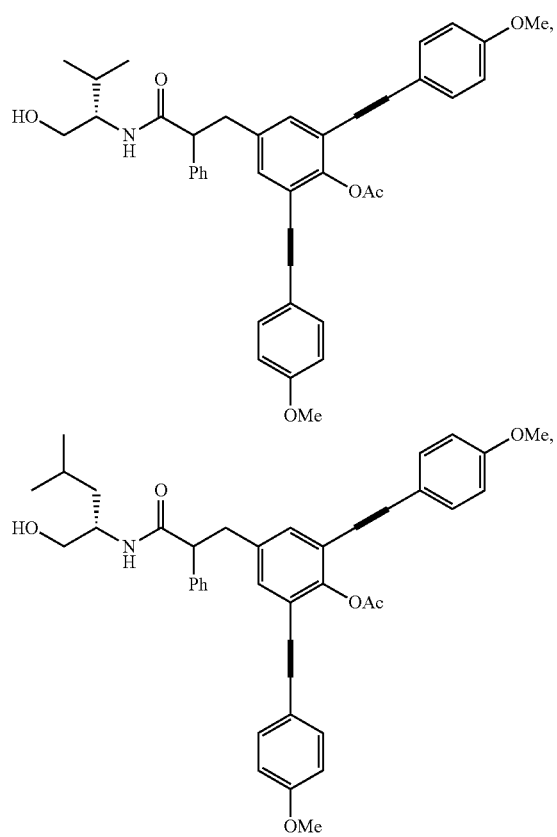
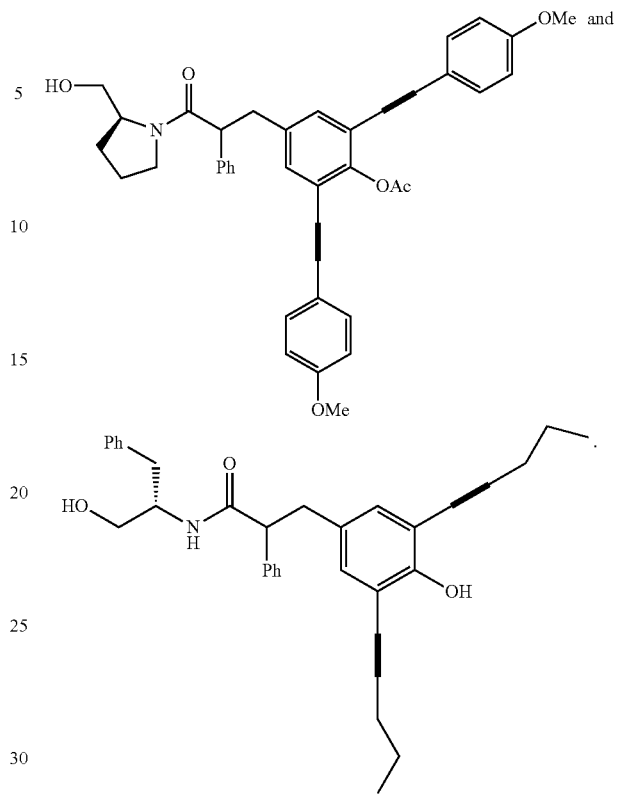
* * * * *